US008811790B2

(12) United States Patent
Niederberger et al.

(10) Patent No.: US 8,811,790 B2
(45) Date of Patent: Aug. 19, 2014

(54) METHOD FOR MANUFACTURING AN OPTICAL WAVEGUIDE, OPTICAL WAVEGUIDE, AND SENSOR ARRANGEMENT

(75) Inventors: Hans-Peter Niederberger, Unken (AT); Josef Schuller, Salzburg (AT); Gottfried Reiter, Adnet (AT)

(73) Assignee: Sony DADC Austria AG, Anif (AU)

( * ) Notice: Subject to any disclaimer, the term of this patent is extended or adjusted under 35 U.S.C. 154(b) by 372 days.

(21) Appl. No.: 12/988,421

(22) PCT Filed: Feb. 18, 2009

(86) PCT No.: PCT/EP2009/001145
§ 371 (c)(1),
(2), (4) Date: Jan. 3, 2011

(87) PCT Pub. No.: WO2009/132726
PCT Pub. Date: Nov. 5, 2009

(65) Prior Publication Data
US 2011/0112769 A1 May 12, 2011

(30) Foreign Application Priority Data

Apr. 18, 2008 (EP) ..................... 08007662

(51) Int. Cl.
*G02B 6/02* (2006.01)
(52) U.S. Cl.
USPC .............................. 385/131; 702/1
(58) Field of Classification Search
USPC .............. 385/1, 129, 14, 50; 702/1, 159, 172; 250/200
See application file for complete search history.

(56) References Cited

U.S. PATENT DOCUMENTS

| 4,749,245 | A | | 6/1988 | Kawatsuki et al. |
| 4,847,132 | A | | 7/1989 | Takao et al. |
| 4,943,131 | A | | 7/1990 | Taki |
| 5,011,248 | A | | 4/1991 | Taki |
| 5,650,992 | A | | 7/1997 | Ohkubo |
| 5,675,691 | A | | 10/1997 | Edlinger et al. |
| 5,940,568 | A | * | 8/1999 | Losch ........................... 385/129 |

(Continued)

FOREIGN PATENT DOCUMENTS

| CH | 688 165 | 5/1997 |
| CN | 1854776 A | 11/2006 |

(Continued)

OTHER PUBLICATIONS

European Office Action issued Mar. 15, 2013, in European Patent Application No. 08 007 662.3.

(Continued)

*Primary Examiner* — Sujoy Kundu
*Assistant Examiner* — Corey Bailey
(74) *Attorney, Agent, or Firm* — Oblon, Spivak, McClelland, Maier & Neustadt, L.L.P.

(57) ABSTRACT

A method for manufacturing an optical waveguide, in which a waveguide structure including a waveguide layer of ZnS—$SiO_2$ is deposited on a first layer, wherein a first refractive index of the first layer is lower than the refractive index of the waveguide layer. A sensor arrangement includes a planar optical waveguide, a light source, a sensor, an application unit for applying an analyte on top of the planar waveguide and a processor connected to the sensor.

19 Claims, 5 Drawing Sheets

(56) References Cited

U.S. PATENT DOCUMENTS

| | | | |
|---|---|---|---|
| 5,998,851 A * | 12/1999 | Nishikata | 257/436 |
| 6,067,393 A * | 5/2000 | Kitaoka et al. | 385/49 |
| 6,146,733 A | 11/2000 | Inoue et al. | |
| 6,240,226 B1 * | 5/2001 | Presby et al. | 385/42 |
| 6,312,780 B1 | 11/2001 | Kasami et al. | |
| 6,469,785 B1 | 10/2002 | Duveneck et al. | |
| 6,483,096 B1 * | 11/2002 | Kunz et al. | 250/214 R |
| 6,493,072 B1 * | 12/2002 | Medberry et al. | 356/73.1 |
| 6,589,712 B1 * | 7/2003 | Hsu | 430/313 |
| 7,151,738 B2 * | 12/2006 | Peng | 369/112.27 |
| 7,897,068 B2 * | 3/2011 | Hosono et al. | 252/519.51 |
| 2004/0252622 A1 * | 12/2004 | Kariyada | 369/275.2 |
| 2005/0053348 A1 * | 3/2005 | Tatehata et al. | 385/129 |
| 2005/0084799 A1 * | 4/2005 | Yahagi et al. | 430/270.11 |
| 2006/0110569 A1 | 5/2006 | Yashiro et al. | |
| 2006/0165945 A1 * | 7/2006 | Kobayashi et al. | 428/64.4 |
| 2007/0183048 A1 | 8/2007 | Riant et al. | |
| 2010/0227773 A1 * | 9/2010 | Abel et al. | 506/9 |
| 2010/0320363 A1 * | 12/2010 | Schleipen | 250/200 |

FOREIGN PATENT DOCUMENTS

| | | |
|---|---|---|
| EP | 0 228 886 | 7/1987 |
| EP | 0 323 317 | 7/1989 |
| EP | 0 533 074 | 3/1993 |
| EP | 0 759 159 | 2/1997 |
| EP | 0 760 944 | 3/1997 |
| EP | 0 938 656 | 9/1999 |
| EP | 1 096 484 | 5/2001 |
| EP | 1 250 618 | 10/2002 |
| EP | 1 371 747 | 12/2003 |
| EP | 1 561 765 | 8/2005 |
| EP | 1 602 968 | 12/2005 |
| EP | 1 626 400 | 2/2006 |
| EP | 1310953 B1 * | 5/2006 |
| JP | 57 173804 | 10/1982 |
| JP | 61-204545 A | 9/1986 |
| JP | 63-103453 A | 5/1988 |
| JP | 1-118105 A | 5/1989 |
| JP | 2002-162345 A | 6/2002 |
| JP | 2005-17429 A | 1/2005 |
| JP | 2005-77315 A | 3/2005 |
| JP | 2008-59684 A | 3/2008 |
| WO | 96 35940 | 11/1996 |
| WO | 98 09156 | 3/1998 |

OTHER PUBLICATIONS

Mikael Mulot: "Planar Waveguides", Helsinki University of Technology, (Apr. 12, 2007).

International Search Report issued Jun. 3, 2009 in PCT/EP09/01145 filed Feb. 18, 2009.

European Office Action issued Jan. 31, 2012 in patent application No. 08 007 662.3.

Kenith E. Meissner, et al., "Optical Characterization of Quantum Dots Entrained in Microstructured Optical Fibers", Physica E vol. 26, No. 1-4, XP004748652, Feb. 1, 2005, pp. 377-381.

Office Action issued Aug. 1, 2012 in European Patent Application No. 08 007 662.3.

Y Zhu, et al. "Room temperature visible photoluminescence from undoped ZnS nanoparticles embedded in $SiO_2$ matrices", Journal of Applied Physics, vol. 92, No. 11, XP012056707, Dec. 1, 2002, pp. 6828-6832.

N. Taghavinia, et al., "ZnS nanocrystals embedded in $SiO_2$ matrix", Physica E, No. 21, Feb. 28, 2004, pp. 96-102.

Office Action issued Aug. 28, 2012 in Japanese Patent Application No. 2011-505378 with English language translation.

Chinese Office Action Issued May 11, 2012 in Patent Application No. 200980113509.4 (English translation only).

* cited by examiner

METHOD FOR MANUFACTURING AN OPTICAL WAVEGUIDE, OPTICAL WAVEGUIDE, AND SENSOR ARRANGEMENT

An embodiment of the invention relates to a method for manufacturing an optical waveguide. Further embodiments of the invention relate to an optical waveguide and to a sensor arrangement, respectively.

BACKGROUND

A waveguide is a spatially inhomogeneous structure for guiding light, i.e. for restricting the spatial region in which light can propagate. This can be used e.g. for transmitting light over long distances (e.g. in telecommunication systems), for guiding light on integrated optical chips (silicon photonics), for maintaining high optical intensities of appreciable lengths (e.g. in waveguide lasers and frequency doublers), for stripping off higher-order transverse modes, for interaction of the guided light with material in the evanescent field (e.g. in certain waveguide sensors), or for splitting and combining beams. Usually, a waveguide contains a region of increased refractive index, compared with a surrounding medium. However, guidance is also possible by the use of reflections e.g. at metallic interfaces.

There are many different techniques for fabricating waveguides. Some examples are lithographic techniques, used with semiconductor, crystal and glass materials, in combination, e.g. with ion exchange or thermal interfusion, fiber fabrication by drawing from a pre-form, drawing fibers into waveguides of further reduced dimensions, resulting in nanowires, writing of waveguides in transparent media with focused and pulsed laser beams, exploiting laser-induced break-down and epitaxial and polishing methods for fabrication of planar waveguides. The trade-offs between different fabrication techniques can be complicated. They can involve aspects like cost, flexibility and reproducibility of manufacturing, achieved propagation losses, possible side effects on the material (e.g. via heating or undiffused materials), optimum mode size and symmetry for coupling to other waveguides.

Planar waveguides are waveguides with a planar geometry. They are often fabricated in the form of a thin transparent film or layer with increased refractive index on some substrate, or possibly embedded between two substrate layers.

Thus, there is still a need for further material systems which provide reliable methods to produce optical waveguides with low absorption loss.

The object is solved by a method, an optical waveguide structure, and a sensor arrangement according to claims 1, 12 and 18 respectively.

Further embodiments are defined in the dependent claims.

Further details of the invention will become apparent from the consideration of the drawings and ensuing description.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

In the following, embodiments of the invention are described. It is important to note, that all described embodiments in the following may be combined in any way, i.e. there is no limitation that certain described embodiments may not be combined with others.

Figure 1:
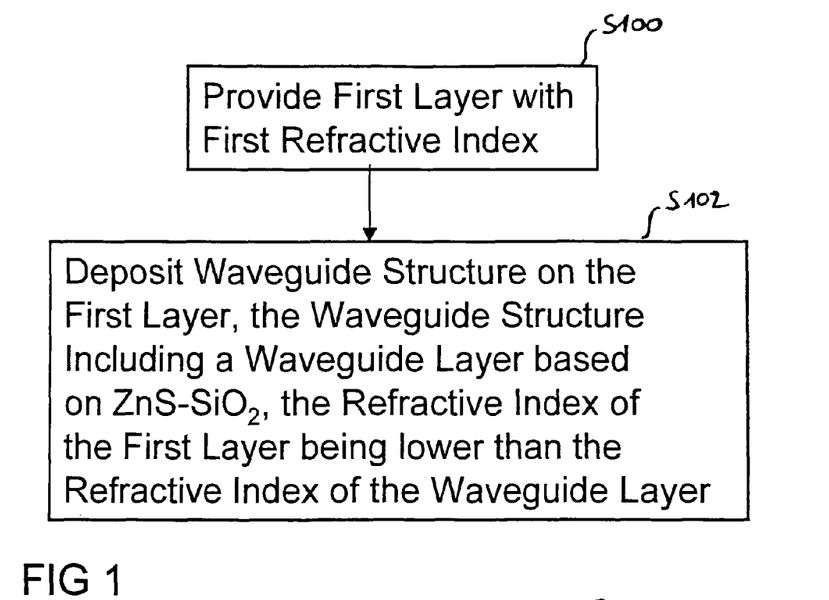
FIG. 1 shows main steps of one embodiment of the invention.

In FIG. 1, in step S100 the first layer with the first refractive index is provided.

In a step S102 a waveguide structure, which includes a waveguide layer which is built from zinc sulfide (ZnS)-silicon dioxide ($SiO_2$), is deposited on the first layer, the refractive index of the first layer being lower than the refractive index of the waveguide layer. The material zinc sulfide-silicon dioxide ZnS—$SiO_2$ might also be referred to as $(ZnS)_{100-x}$—$(SiO_2)_x$, wherein x specifies the weight percentage of silicon-dioxide.

Figure 2:
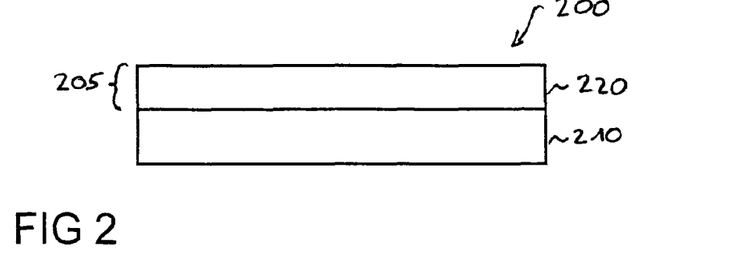
FIG. 2 shows a cross-section of an optical waveguide according to a further embodiment of the invention.

With this method an optical waveguide 200, as it is depicted in FIG. 2 in a cross-sectional view is obtained. The waveguide structure 205 includes a waveguide layer 220. In the depicted embodiment there is no further layer within the waveguide structure 205, however, as is explained with respect to further embodiments below, the waveguide structure 205 might include further layers. In case when the refractive index of the first layer 210 is lower than the refractive index of the waveguide layer 220, light which is coupled into the waveguide layer 220 will remain within the waveguide layer 220 and might be guided without significant loss, if the absorption coefficient of the waveguide layer 220 is low.

Figure 8A:
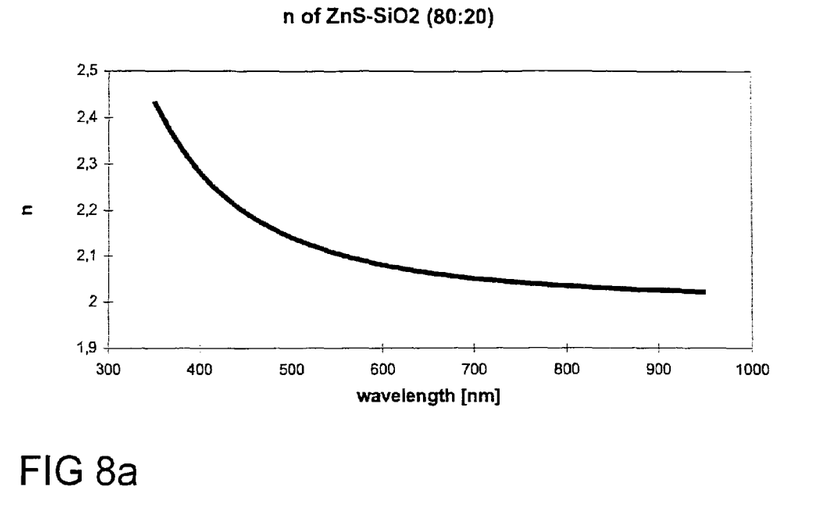
FIG. 8*a* shows a viewgraph depicting the wavelength-dependency of the refractive-index of an embodiment of a ZnS—SiO2 waveguide.
Figure 8B:
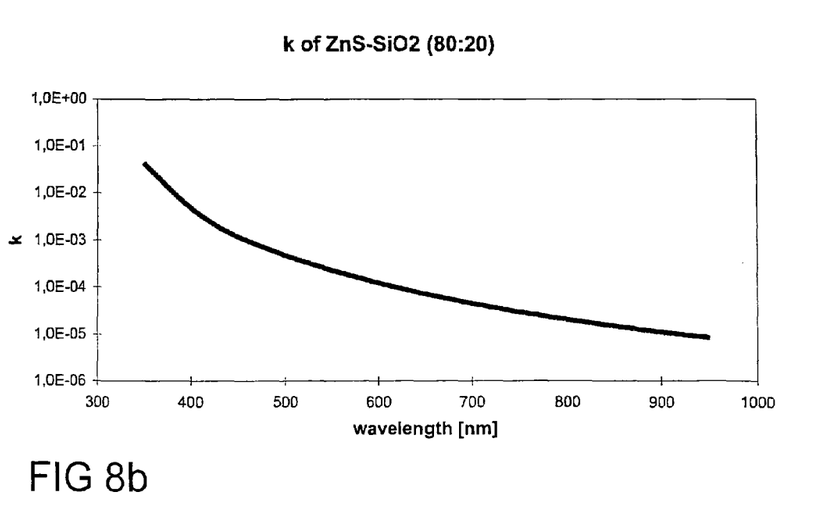
FIG. 8*b* shows a viewgraph depicting the wavelength-dependency of the absorption coefficient of an embodiment of a ZnS—SiO2 waveguide.

The material system of ZnS—$SiO_2$, which is used for the waveguide layer, shows a low absorption coefficient for wavelength in the visible region and in the near infrared region as it is depicted in FIG. 8*b*. ZnS—$SiO_2$ is a mixture of two components, i.e. zinc sulfide, which might be present as small crystalline grains and non-crystalline silicon dioxide. The refractive index of this material system is dependent on the amount of ZnS or $SiO_2$, respectively. If more $SiO_2$ is present, the refractive index is lower. In the visible light region the refractive index of pure ZnS is around 2.3 and decreases approximately linearly to 1.85 for a material system of 50% ZnS and 50% $SiO_2$.

The first layer 210 might be a substrate, so that e.g. a two-layer system is provided. The substrate might be made of glass or of a polymer, which both have a refractive index below the refractive index of ZnS—$SiO_2$. The substrate might be realized from one material, but it is also possible that the substrate might comprise a plurality of different layers, wherein the uppermost layer, i.e. the layer in contact with the waveguide structure 205 has a refractive index lower than the refractive index of the waveguide layer.

The first layer may also be a silicon based material, e.g. Silicon-Oxy-Nitride (SiON), SiCON or SiCO2 or the like.

Figure 3:
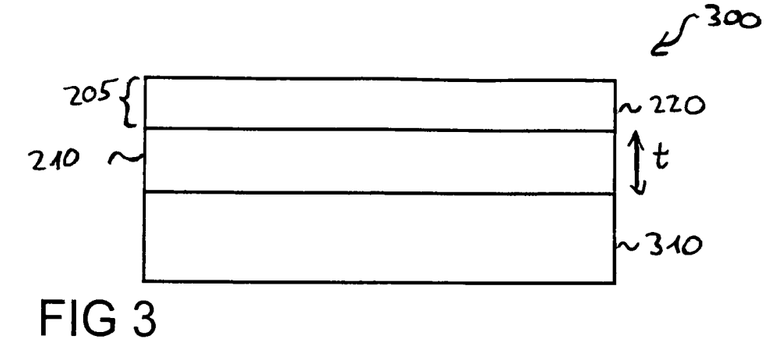
FIG. 3 shows a cross-section of an optical waveguide according to a further embodiment of the invention.

In FIG. 3 an optical waveguide 300 is depicted which results from depositing the first layer 210 on a further substrate 310 before depositing the waveguide layer 220 or the waveguide structure 205 on top of the first layer 210. Within this embodiment the first layer 210 acts as an intermediate layer between the waveguide layer 220 or the waveguide structure 205 and the further substrate 310. Some of the materials, which might be used as the further substrate 310, e.g. certain polymers like poly-carbonate (PC) might have a large absorption for a used wavelength. With an additional intermediate layer 210 disposed between the further substrate 310 and the waveguide layer 220 or the waveguide structure 205, the absorption loss within the waveguide layer 220 or the waveguide structure 205 might be adjusted by choosing the thickness t of the first layer 210 appropriately. The first layer should have a low absorption coefficient for the used wavelength of light within the waveguide layer 220 or the waveguide structure 205. A possible material for the first layer 210 is $SiO_2$, which has a low absorption coefficient and which is easy the deposit onto substrates made of glass, silicon or polymers.

The substrate 310 might be made of a semiconductor material, or of glass or of a polymer (plastics).

Since the refractive index of ZnS—$SiO_2$ might be above 2.0, e.g. for $SiO_2$, amounts below around 30%, the first refractive index of the first layer 210 might be chosen between 1.3 and 2.0, or between 1.4 and 1.8 or between 1.4 and 1.6. In each case, the condition that the refractive index of the first layer 210 is below the refractive index of the waveguide layer of ZnS—$SiO_2$ is fulfilled.

The waveguide layer or the waveguide structure might be deposited on top of the first layer 210 by a physical vapor deposition process, e.g. by a sputtering process, which is inexpensive and fast. With sputtering the deposition rates of more than 2 nm/s might be achieved which is larger than deposition rates of other comparable waveguide materials like $Ta_2O_5$ and $TiO_2$. The attenuation of the ZnS—$SiO_2$ based waveguide structures or waveguide layers is comparable to $Ta_2O_5$ and $TiO_2$ layers deposited by evaporation processes.

Within the sputtering process targets built from ZnS or ZnS—$SiO_2$ might be used.

With a commercially available sputter system using a typical power of 4.5 kW and a ZnS-sample a thickness uniformity of the waveguide layer of ±2.5% is achievable on a substrate diameter of 120 mm and a rate of around 13 nm/s. If smaller substrates are used, the better values for the uniformity are possible. A refractive index uniformity of ±0.11% might be achieved with the sputtering process.

It is also possible to deposit the waveguide layer or the waveguide structure by an ion plating process, which is very precise or by chemical vapor deposition processes or plasma enhanced chemical vapor deposition processes.

The content of ZnS in the waveguide layer 220 might be between 10% and 95%, or between 50% and 90% or between 70% and 90%. Material systems with the content of zinc sulphide with less than 100% are less brittle and thus easier to handle.

Figure 4:
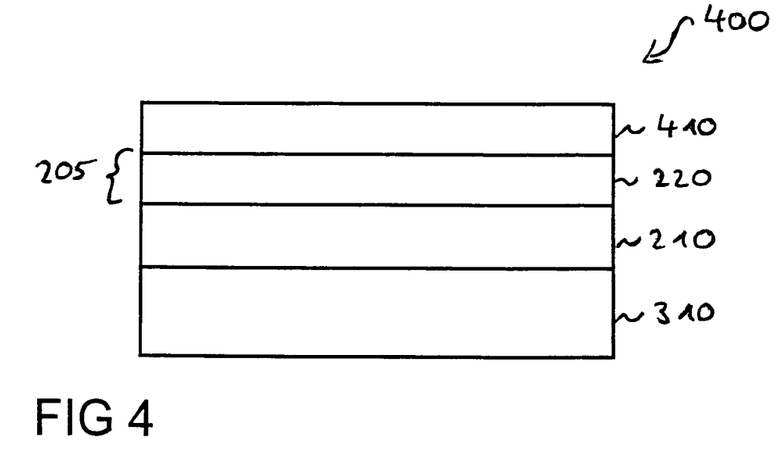
FIG. 4 shows a cross-section of still a further embodiment of an optical waveguide.

In FIG. 4 a further embodiment of an optical waveguide 400 is depicted, which comprises a cladding layer 410 of a second material with a second refractive index on top of the waveguide layer 220 or the waveguide structure 205, wherein the second refractive index is lower than the refractive index of the waveguide layer 220. The cladding layer 410 ensures that the waveguide layer 220 or the waveguide structure 205 is disposed between two layers (i.e. the first layer 210 and the second layer 410) which both have refractive indexes that are lower than the refractive index of the waveguide layer. In addition, the cladding layer 410 might be used to protect the waveguide layer 220 or the waveguide structure 205 against physical destruction, e.g. by stretching or shocks. A cladding layer might e.g. be used as well for protection against chemical effects like corrosion or as an adhesion promoter for further layers or for reducing the surface roughness. A cladding layer 410 might consist of one layer or multiple sub-layers. The thickness of the cladding layer 410 is not limited.

The optical waveguides 200, 300 and 400 are depicted in FIGS. 2, 3 and 4 as planar waveguide structures, which guide the light in one dimension, i.e. the direction in which the layers are stacked on top of each other. The light can only propagate in the waveguide layer or the waveguide structure.

However, it might be possible as well to use the waveguide structures built from ZnS—$SiO_2$ which are further structured, e.g. as rib waveguides, which are able to guide the light also in a further direction for example substantially perpendicular to the one dimension in which light is guided in planar waveguides.

Figure 5:
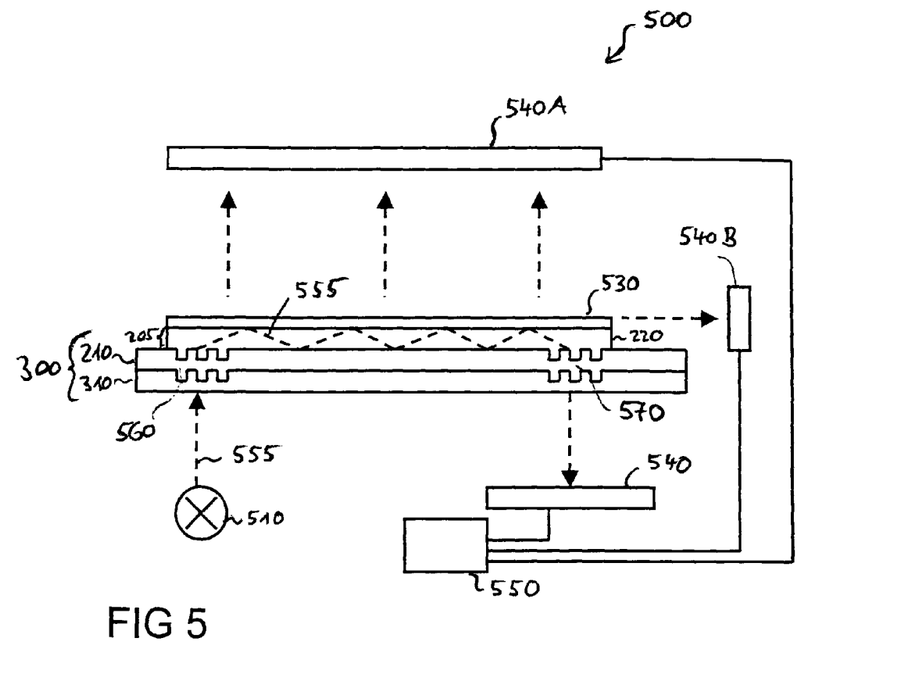
FIG. 5 shows schematically a sensor arrangement according to a further embodiment of the invention.

In FIG. 5 a sensor arrangement 500 is depicted which comprises an optical waveguide 300 including a substrate 310, a first layer 210 and a waveguide layer 220 or waveguide structure 205 in which the refractive index of the first layer 210 is lower than the refractive index of the waveguide layer 220. The waveguide layer 220 is made from ZnS—$SiO_2$ with the refractive index above 2.0. The sensor arrangement further comprises a light source 510, a sensor 540 and/or further sensors 540A and/or 540B and a processor 550 which is connected to the sensor 540 or to a plurality of sensors 540, 540A, 540B. On top of the waveguide layer 220 or the waveguide structure 205 an analyte 530 is applied.

Light 555 from the light source 510 is coupled into the waveguide layer 220 or the waveguide structure 205 by an optical diffraction grating 560 and guided through the waveguide layer 220 or the waveguide structure 205. In the region where the analyte 530 contacts the surface of the waveguide layer 220 or the waveguide structure 205 a part of the light 555 is present as a so-called evanescent field within the analyte 530.

A second diffraction grating 570 might be provided for coupling out the light 555 and in order to detect the outcoupled light with the sensor 540, resulting in an auxiliary signal forwarded to the processor 550. The auxiliary signal depends on characteristics of the analyte (e.g. its concentration) and therefore, might be used to determine such characteristics. Optionally, light that is coupled out from the analyte might be directly received by further sensors 540A, 540B.

Other embodiments for coupling in the light 555 into the waveguide layer 220 or the waveguide structure 205 might comprise prisms for incoupling the light or edge-coupling schemes.

The term analyte should be understood within the context of this description as a substance which is to be analyzed by itself or as a system, which comprises the substance that is to be analyzed. The detection can be effected in a one-step or multiple-step assay during the course of which the surface of the waveguide layer 220 or the waveguide structure 205 is brought into contact with one or more solutions. One of the solutions used might comprise a luminescent substance which can be detected. If a luminescent substance has already been adsorbed onto the waveguide region, the analyte may also be free of luminescent constituents. The analyte may contain further constituents, such as pH buffers, salts, acids, bases, surfactants, viscosity-influencing additives or dyes.

The analyte may be a biological medium, such as egg yolk, a body fluid or the components thereof, especially blood, serum, plasma or urine. It may also be surface water, solutions or extracts from natural or synthetic media, such as soils or parts of plants, liquors from biological processes or synthetic liquors. The analyte may be used either undiluted or with added solvent.

The light can be detected as well at different positions, e.g. the emitted light from the luminescent substances or scattered light might be detected directly or light emitted from the waveguide layer or the waveguide structure at the edges of the waveguide layer or the waveguide structure might be detected, etc.

As luminescent compounds functionalized luminescent dyes (e.g. dyes including rhodamines, fluorescein derivatives, etc.) having a luminescence of a wavelength in the range of 330 nm to 1000 nm might be used.

The use of different fluorescent dyes that can all be excited by light of the same wavelength, but have different emissions wavelengths, may be advantageous.

The analytes can either be brought into contact with the waveguide structure 205 when stationary or be passed over them continuously, it being possible for the circulation to be open or closed.

The evanescently excited luminance or scattered light or loss of light intensity can be detected by photodiodes, photocells, photomultipliers, CCD cameras and detector arrays, like CCD rows or CCD arrays. The light can be projected onto the latter by means of optical elements, such as mirrors, prisms, lenses, Fresnel lenses and graded-index lenses in order to detect it.

Figure 6:
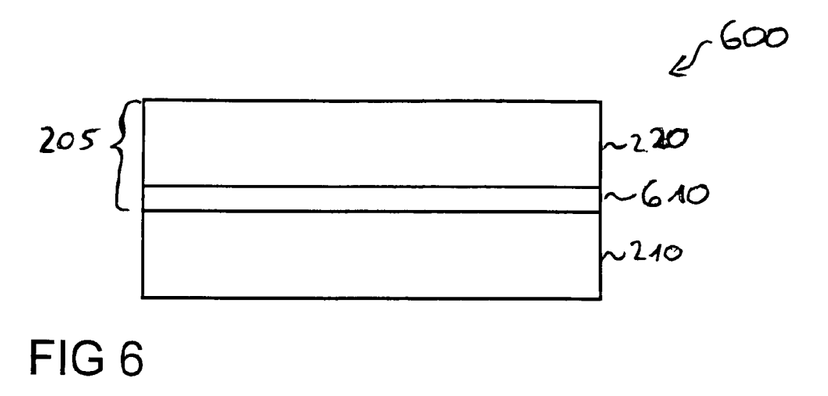
FIG. 6 shows a cross-section of still a further embodiment of an optical waveguide.

In FIG. 6 a further embodiment of an optical waveguide 600 is depicted. As already stated above the waveguide structure 205 might include one or more further layers in addition to the waveguide layer 220. In this embodiment an intermediate layer 610 is formed between the waveguide layer 220 and the first layer 210. This intermediate layer 610 might enhance the adhesion of the waveguide structure 205 to the first layer 210 or might improve the surface characteristics like roughness. The intermediate layer 610 might consist of one layer or multiple sub-layers.

Figure 7:
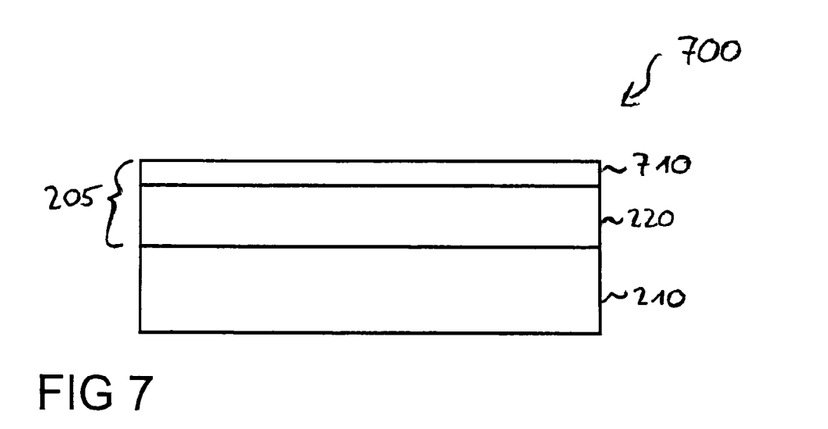
FIG. 7 shows a cross-section of still a further embodiment of an optical waveguide.

In FIG. 7 still a further embodiment of an optical waveguide 700 is depicted. In this embodiment the waveguide structure 205 includes a further layer 710 on top of the waveguide layer 220. The further layer 710 e.g. might be used e.g. to adapt the surface properties like surface tension, surface roughness, improve the abrasion resistance or to protect the waveguide layer 220 against chemicals used as analytes 530 in the sensor arrangement of FIG. 5. The further layer 710 might be an optical transparent material, which has a low absorption coefficient in the used wavelength region. For instance, a thin layer of $Ta_2O_5$ (Tantalum Pentoxide) with a refractive index of approximately 2.1 might be used as the further layer 710. The optical characteristics of this waveguide structure 205 are comparable to the optical characteristics of a single ZnS—$SiO_2$-based waveguide layer 220, but the chemical resistance is improved. Other possible material systems for the further layer 710 might comprise but are not restricted to $TiO_2$ (titanium dioxide), $Si_3N_4$ (silicon nitride) or $SiO_2$ (silicon-dioxide). The further layer 710 might consist of one layer or multiple sub-layers.

The thickness of the further layer 710 is depending on the required functionality but in most cases it should be as small as possible so that it does not disturb the functionality of the waveguide. For instance, in order to improve the chemical resistance of a ZnS—$SiO_2$-based waveguide layer 220 a 10 nm layer of $Ta_2O_5$ as a further layer 710 can be sufficient, depending on the chemistry used. Thus, the thickness of the further layer 710 might be chosen be between 1 and 100 nm, preferably between 2 and 20 nm.

The materials used for the further layer 710 might be used as well for the intermediate layer 610. It is also possible that the waveguide structure includes an intermediate layer 610 and a further layer 710 in addition to the waveguide layer 220.

In FIG. 8a a measured relation of the refractive index in dependence of the wavelength of inputted light is depicted. The values have been measured on a sample with a thickness of the waveguide layer of 60 nm and a ratio of ZnS to SiO2 of 80:20 (wt %). The viewgraph shows a decrease of the refractive index from n=2.4 at a wavelength of 350 nm to an index n=2 at a wavelength of 950 nm.

In FIG. 8b a measured relation of the absorption coefficient k in dependence of the wavelength of the inputted light is depicted. The values have been measured on the same sample as in FIG. 8a, i.e. with a thickness of the waveguide layer of 60 nm and a ratio of ZnS to SiO2 of 80:20 (wt %). The viewgraph shows a decrease of the absorption coefficient from $10^{-1}$ at a wavelength of 350 nm to $10^{-5}$ at a wavelength of 950 nm.

A novel optical waveguide and method for manufacturing the optical waveguide is provided, which results in a low absorption loss optical waveguide with high deposition rate, thus efficiently reducing manufacturing costs of such optical waveguides.

The invention claimed is:

1. An optical waveguide, comprising:
    a substrate;
    a first layer with a first refractive index formed directly on top of the substrate; and
    a waveguide structure formed directly on top of the first layer,
    wherein the waveguide structure includes a waveguide layer which includes ZnS—$SiO_2$, the waveguide layer having a higher refractive index than the first refractive index of the first layer,
    wherein a light beam coupled into the waveguide layer is guided within the waveguide layer such that the light beam travels along a predefined path volume formed by the waveguide layer, and
    wherein the first layer has a first absorption coefficient with respect to a wavelength of light guidable in the waveguide layer, and the substrate has a second absorption coefficient with respect to the wavelength of light guidable in the waveguide layer, the first absorption coefficient being less than the second absorption coefficient.

2. An optical waveguide according to claim 1, wherein the substrate is made of one of glass, of a polymer, and of a semiconductor material.

3. An optical waveguide according to claim 1, wherein the first layer is made of one of glass, of $SiO_2$, of a semiconductor material, and of a polymer.

4. An optical waveguide according to claim 1, further comprising:

a cladding layer with a second refractive index, wherein the waveguide structure is sandwiched between the cladding layer and the first layer and the second refractive index is lower than the refractive index of the waveguide layer.

5. An optical waveguide according to claim 1, wherein the waveguide structure includes a further layer formed on top of the waveguide layer.

6. A sensor arrangement, comprising:
a planar optical waveguide including:
    a substrate,
    a first layer with a first refractive index formed directly on top of the substrate, and
    a planar waveguide structure formed directly on top of the first layer,
    wherein said waveguide structure includes a waveguide layer which includes $ZnS$—$SiO_2$, and which has a higher refractive index than the first refractive index of the first layer,
    wherein light coupled into the waveguide layer is guided within the waveguide layer, and
    wherein the first layer has a first absorption coefficient with respect to a wavelength of light guidable in the waveguide layer, and the substrate has a second absorption coefficient with respect to the wavelength of light guidable in the waveguide layer, the first absorption coefficient being less than the second absorption coefficient;
a light source configured to provide light at the wavelength of light guidable by the waveguide layer to be coupled into the planar optical waveguide;
a sensor configured to detect an auxiliary signal based on said light; and
a processor connected to said sensor, said processor being configured to determine predetermined parameters of an analyte applied on top of the planar optical waveguide by evaluating said auxiliary signal.

7. A method for manufacturing an optical waveguide, comprising:
providing a substrate;
providing a first layer with a first refractive index directly on top of the substrate; and
depositing a waveguide structure directly on top of the first layer,
wherein the waveguide structure includes a waveguide layer of $ZnS$—$SiO_2$, and the first refractive index of the first layer is lower than a refractive index of the waveguide layer,
wherein the waveguide layer is configured such that a light beam at a predetermined wavelength coupled into the waveguide layer is guided within the waveguide layer such that the light beam travels along a predefined path volume formed by the waveguide layer, and
wherein the first layer has a first absorption coefficient with respect to the light beam at the predetermined wavelength, and the substrate has a second absorption coefficient with respect to the light beam at the predetermined wavelength, the first absorption coefficient being less than the second absorption coefficient.

8. A method according to claim 7, wherein the first layer is a substrate made of one of glass, of a polymer, and of a semiconductor material.

9. A method according to claim 7, further comprising:
depositing the first layer on the substrate before said depositing the waveguide structure.

10. A method according to claim 9, wherein the substrate is made of one of glass, a polymer, and a semiconductor material.

11. A method according to claim 7, wherein first layer is made of $SiO_2$.

12. A method according to claim 7, wherein said depositing the waveguide structure is performed by a process from the group of a physical vapor deposition process, an ion plating process, an evaporation process, a chemical vapor deposition process, a plasma enhanced chemical vapor deposition process, and a sputtering process.

13. A method according to claim 7,
wherein said depositing the waveguide structure is performed by a sputtering process, and
wherein one of a ZnS-target and a $ZnS$—$SiO_2$-target is used during the sputtering process.

14. A method according to claim 7, wherein the content of ZnS in the waveguide layer is between 70% and 90%.

15. A method according to claim 7, wherein during said depositing the waveguide structure a further layer is deposited on the waveguide layer.

16. A method according to claim 7, further comprising:
depositing a cladding layer of a second material with a second refractive index on top of the waveguide structure,
wherein the second refractive index is lower than the refractive index of the waveguide layer.

17. An optical waveguide according to claim 1, wherein the waveguide layer includes $ZnS$—$SiO_2$ according to $(ZnS)_{100-x}$—$(SiO_2)_x$, where x is the weight percentage of $SiO_2$ and is in a range between 10 and 50.

18. A sensor arrangement according to claim 6, wherein the waveguide layer includes $ZnS$—$SiO_2$ according to $(ZnS)_{100-x}$—$(SiO_2)_x$, where x is the weight percentage of $SiO_2$ and is in a range from 10 to 50.

19. An optical waveguide according to claim 1, wherein an upper side of the waveguide structure opposite a side thereof formed directly on top of the first layer is exposed and without another layer formed thereon.

* * * * *